United States Patent
Grobler et al.

(10) Patent No.: US 10,308,929 B2
(45) Date of Patent: Jun. 4, 2019

(54) METHOD OF PREPARING BIOLOGICAL MATERIAL

(75) Inventors: Anne Frederica Grobler, Potchefstroom (ZA); Oksana Levanets, Potchefstroom (ZA)

(73) Assignee: North-West University, Potchefstroom (ZA)

( * ) Notice: Subject to any disclaimer, the term of this patent is extended or adjusted under 35 U.S.C. 154(b) by 565 days.

(21) Appl. No.: 14/343,019

(22) PCT Filed: Sep. 6, 2012

(86) PCT No.: PCT/IB2012/054608
§ 371 (c)(1),
(2), (4) Date: Jun. 16, 2014

(87) PCT Pub. No.: WO2013/035062
PCT Pub. Date: Mar. 14, 2013

(65) Prior Publication Data
US 2014/0370508 A1  Dec. 18, 2014

(30) Foreign Application Priority Data

Sep. 6, 2011  (ZA) ............................. 2011/06492

(51) Int. Cl.
*C12N 15/10* (2006.01)
*C12Q 1/6806* (2018.01)
*G01N 33/543* (2006.01)
*G01N 1/34* (2006.01)

(52) U.S. Cl.
CPC ..... *C12N 15/1003* (2013.01); *C12N 15/1006* (2013.01); *C12Q 1/6806* (2013.01); *G01N 1/34* (2013.01); *G01N 33/54386* (2013.01); *Y10T 436/255* (2015.01)

(58) Field of Classification Search
CPC ................................................ C12N 15/1003
USPC ....................................................... 536/25.4
See application file for complete search history.

(56) References Cited

U.S. PATENT DOCUMENTS

| | | | |
|---|---|---|---|
| 5,346,994 A | 9/1994 | Chomczynski | |
| 6,084,091 A * | 7/2000 | Muller | C12N 15/1006 435/6.14 |
| 6,348,318 B1 * | 2/2002 | Valkirs | C07K 16/1282 435/7.1 |
| 2010/0291536 A1 | 11/2010 | Viljoen et al. | |

FOREIGN PATENT DOCUMENTS

| | | |
|---|---|---|
| WO | WO-2004099384 A2 | 11/2004 |
| WO | WO-2006023471 A2 | 3/2006 |
| WO | WO-2010015835 A1 | 2/2010 |
| WO | WO-2013035062 A1 | 3/2013 |

OTHER PUBLICATIONS

"International Application Serial No. PCT/IB2012/054608, International Search Report dated Jan. 30, 2013", 3 pgs.
Boom, R., et al., "Rapid and simple method for purification of nucleic acids", J. Clin. Microbiol., 28, (1989), 495-503.
Bush, Chris, et al., "Rapid Isolation of Genomic DNA from Whole Blood by Binding to Borosilicate Particles", Clinical Chemistry 37(6), Abstracts of Meeting Papers, (Jun. 1991), 1060.

* cited by examiner

*Primary Examiner* — Jezia Riley
(74) *Attorney, Agent, or Firm* — Schwegman Lundberg & Woessner, P.A.

(57) ABSTRACT

This invention pertains to a method of preparing biological material from a biological sample selected from the group consisting of blood and sputum samples. The method includes the step of altering at least one constitutive characteristic of the biological sample in the presence of a capturing scaffold by adding a lysis buffer containing a solubilising agent and a detergent to the biological sample, for simultaneously inhibiting coagulation of the biological sample; lysing the biological sample to release the biological material from the biological sample, thus making the biological material available; and capturing at least one fraction of the biological material on the capturing scaffold.

16 Claims, 1 Drawing Sheet

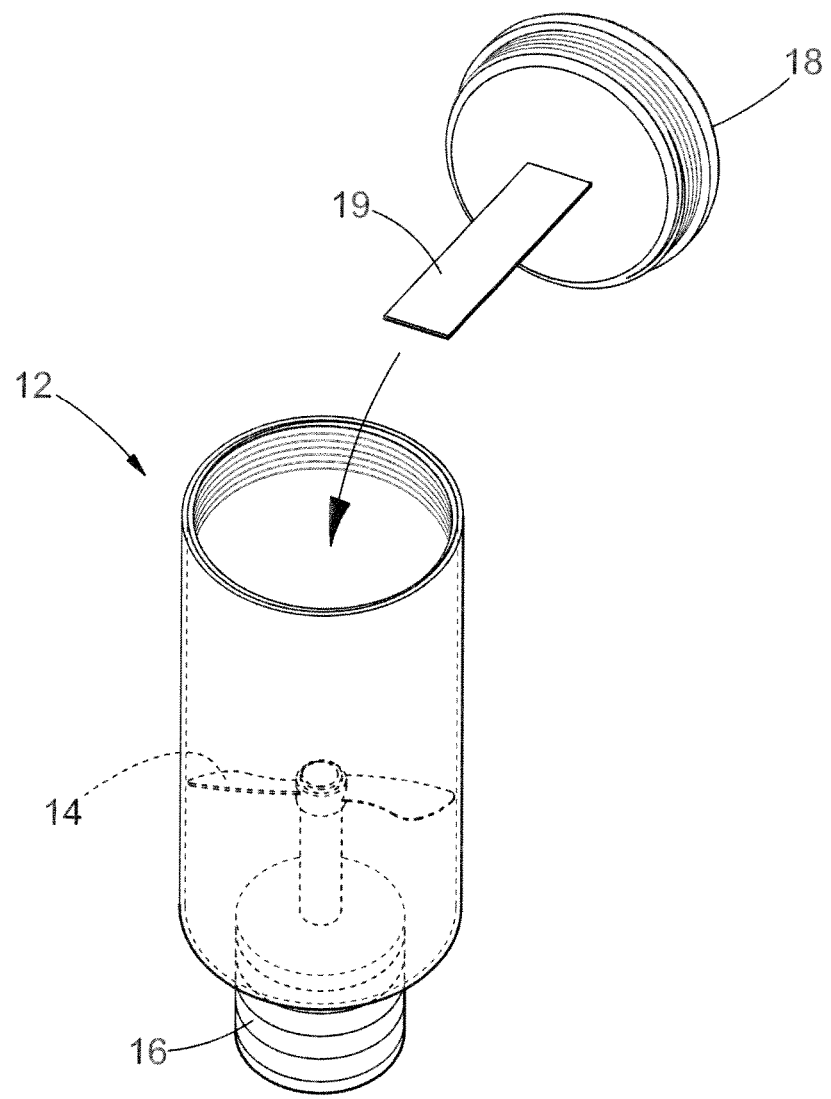

METHOD OF PREPARING BIOLOGICAL MATERIAL

PRIORITY APPLICATIONS

This application is a U.S. National Stage Filing under 35 U.S.C. 371 from International Application No. PCT/IB2012/054608, filed on 6 Sep. 2012 and published as WO/2013/035062 A1 on 14 Mar. 2013, which application claims the benefit of priority to South African Application No. 2011/06492, filed on 06 Sep. 2011; which applications and publication are incorporated herein by reference in their entirety.

INTRODUCTION AND BACKGROUND

This invention relates to a method of preparing biological material obtained from a biological sample, more particularly a blood or sputum sample.

Methods for preparing biological material obtained from blood or sputum samples have been known for decades. These methods are based on multiple steps of preparing and purifying the biological material. For example, normally, the known methods for preparing and purifying nucleic acids include the steps of:
- separating of white cell fraction from the balance of the blood sample through centrifugation;
- lysing the white cell fraction with a detergent;
- digesting the white cell fraction with proteinase;
- extracting the biological material from the digested white cell fraction with organic solvents such as phenol; and
- precipitating the biological material by adding alcohol.

The precipitated biological material is subsequently analysed or stored or transported for later analysis.

A first disadvantage of these methods is thus that, owing to the multiple steps, the methods are laborious and time consuming. Another disadvantage experienced with this method is that the addition of enzymes and reagents in the form of detergents and solvents interferes with the analysis of the biological material. Yet another disadvantage of these methods is that owing to the relative complexity of the steps, and the nature of the reagents used, the implementation of these methods are confined mostly to laboratories and are not suitable to be exercised in the field where blood samples are collected.

A further disadvantage of the known methods of preparing biological material from blood samples is that they require regular manual handling of the samples, thereby increasing risk for laboratory personnel to be infected with hepatitis virus, human immunodeficiency virus (HIV) as well as other pathogens present in the blood samples. Also, it was found that with the known methods, there is an increased risk for cross-sample contamination, potentially leading to false positive results. This could have devastating effects in cases where a person is incorrectly diagnosed with HIV.

Both Boom et al. (1989) and Bush et al. (1991) disclose a method for preparing biological material, such as DNA, by using a strong chaotropic agent, guanidinium thiocyanate (GuSCN), for lysing human cells, and followed by sorbtion of DNA to glass powder. These methods use the ability of glass-based sorbents to bind DNA or nucleic acids at high salt concentrations and release at low salt concentrations.

A disadvantage of the method proposed by Boom et al. (1989) and Bush et al. (1991) is that it consists of multiple steps, including lysing, binding and several washing steps with different buffers and is therefore not suitable for the rapid or immediate preparation of biological material for analysis from the blood samples. In particular, the method is not suitable for preparing nucleic acid material from whole blood samples, owing to the presence of a large amount of proteins in the blood. In addition, without the inclusion of several washing steps, the nucleic acids are contaminated by red blood cells, thereby inhibiting PCR amplification.

Furthermore, various methods of capturing biological material from the biological samples, such as blood and tissue, have been developed and are commercially available. For example, U.S. Pat. No. 5,346,994 discloses a method of isolating substantially pure RNA, DNA and proteins from biological tissue, comprising the steps of:
- (a) homogenising a tissue sample in a solvent solution comprising effective amounts of phenol, a guanidinium compound and a thiocyanate compound selected from the group consisting of ammonium thiocyanate and sodium thiocyanate for extracting substantially pure and undegraded RNA, substantially pure and undegraded DNA, and proteins from biological tissue to form a homogenate;
- (b) adding a water-insoluble organic solvent to said homogenate and sedimenting it to form a mixture consisting of an aqueous phase containing substantially pure, undegraded RNA, an organic phase containing proteins, and an interphase containing substantially pure, undegraded DNA;
- (c) precipitating RNA from the aqueous phase by the addition of a lower alcohol thereto and recovering the precipitated RNA by sedimentation;
- (d) extracting the organic phase and interphase with water;
- (e) precipitating proteins from the organic phase by the addition of a lower alcohol thereto and recovering the precipitated proteins by sedimentation; and
- (f) precipitating DNA from the interphase by the addition of CsCl, sodium citrate solution and a lower alcohol thereto and recovering the precipitated DNA by sedimentation.

From the above it is clear that the method of the above patent is not only time consuming and relatively complex, but also limited to the use of specific enzymes and reagents.

There is therefore clearly a long-standing need for an efficient and robust method for preparing uncontaminated biological material from a blood sample without applying numerous consecutive steps that necessarily have to be taken in a laboratory environment.

US patent application number US2010/0291536A1 ("the '563 application") discloses a method and device for collecting, treating and analysis of biological material by introducing a source material into a specimen container, transferring the source material to a processing device and thermally, chemically and/or mechanically treating the source material to alter at least one constitutive characteristic of the source material and to release or create a target material from the source material. Furthermore, paragraph 23 on page 3 of the specification states that the source material may include blood and sputum, amongst other. However, a disadvantage experienced with the method disclosed in the '563 application, as confirmed by the inventors thereof, was that they were unable to successfully apply the method disclosed in the specification to blood samples.

A further disadvantage of the invention disclosed in the '563 application is that it requires two distinct steps taking place in two separate chambers or wells. The inventors of the present invention thus embarked on research aimed at improving the method disclosed in the '563 application to the extent that it could be successfully applied to blood samples using steps occurring simultaneously in a single chamber.

OBJECTS OF THE INVENTION

It is accordingly an object of the present invention to provide a method for preparing biological material from a biological sample selected from the group consisting of blood and sputum samples with which the aforesaid disadvantages could be overcome or at least minimised and/or to provide a commercially viable alternative to the known methods.

It is a further object of the invention to provide a simple, relatively fast, efficient and robust method for preparing uncontaminated biological material from the biological sample without the need to apply numerous consecutive steps that necessarily have to be taken in a laboratory environment.

It is a further object of the present invention to provide improvements to the invention disclosed in the '536 application so that the method could be successfully applied to the biological sample, more particularly the blood sample.

SUMMARY OF THE INVENTION

According to a first aspect of the invention there is provided a method of preparing biological material from a biological sample selected from the group consisting of blood and sputum samples, the method including the step of altering at least one constitutive characteristic of the biological sample in the presence of a capturing scaffold by adding a lysis buffer containing a solubilising agent and a detergent to the biological sample, for simultaneously:
  inhibiting coagulation of the biological sample;
  lysing the biological sample to release the biological material from the biological sample thus making the biological material available; and
  capturing at least one fraction of the biological material on the capturing scaffold.

Further according to the invention, the step of altering at least one constitutive characteristic of the biological sample in the presence of a capturing scaffold includes the further concomitant steps of:
  physically treating the biological sample through agitation; and
  elevating the temperature of the biological sample above 40 degrees Celsius and up to a 100 degrees Celsius, preferably 92 degrees Celsius.

The method may include the subsequent step of removing the capturing scaffold together with the captured fraction of the biological sample from the remainder of the biological sample.

The solubilising agent may comprise a chaotropic salt in the lysis buffer selected from the group consisting of urea, thiourea, guanidine hydrochloride, lithium perchlorate, sodium iodine, sodium perchlorate, guanidine isothiocyanate, guanidine carbonate, guanidine thiocyanate, derivatives thereof, preferably guanidine hydrochloride and combinations thereof.

The concentration of the chaotropic salt in the lysis buffer may be in the range of from 2M to 8M, preferably from 4M to 6M.

The lysis buffer may be selected from the group consisting of phosphate buffers, 4-(2-hydroxyethyl)-1-piperazineethanesulfonic acid (HEPES), N-Cyclohexyl-2-aminoethanesulfonic acid (CHES), N-cyclohexyl-3-aminopropanesulfonic acid (CAPS) and piperazine-N,N-bis(2-ethanesulfonic acid) (PIPES), Tris-HCl, as well as other tris(hydroxymethyl)aminomethane (Tris) buffers containing ethylene diamine tetra-acetic acid (EDTA), ethylene glycol tetra-acetic acid (EGTA), deoxycholate, sodium chloride (NaCl), sodium phosphate, octylphenoxypolyethoxyethanol, and non-ionic surfactants provided with a hydrophilic polyethylene oxide group and a hydrocarbon lipophilic or hydrophobic group, and combinations thereof.

The lysis buffer may have a pH of between 4 and 12, preferably 6 and 7.5.

The detergent may be selected from the group consisting of 3-[(3-cholamidopropyl)dimethylammonio]-1-propanesulfonate (CHAPS), a nonionic surfactant and emulsifier derived from polyethoxylated sorbitan and oleic acid, a nonionic surfactant which has a hydrophilic polyethylene oxide group and a hydrocarbon lipophilic or hydrophobic group, saponin, sodium deoxycholate, SDS, octyl glucoside, octyl thioglucoside, laurly maltose, octylphenoxypolyethoxyethanol, and combinations thereof.

The detergent may have a concentration of between 0.3% and 6%, preferably 1% and 2%.

The biological material may be captured in the form of nucleic acids, protein, serum, cells, tissue, plasma, antigens, antibodies, or reaction products.

The method may include the step of concomitantly adding a reducing agent selected from the group consisting of 2-mecarptoethanol, dithiothreitol (DTT), 2-mercaptoethylamine, tris(2-carboxyl)phosphine (TCEP), cysteine HCl, N-ethylmaleimide, Nacystelyn, dornase alfa, thymosin $\beta_4$, guaifenesin TCEP HCl, and combinations thereof, to the biological sample together with the lysis buffer containing the solubilising agent and the detergent.

The method may include the concomitant step of adding purified starch to the biological material for neutralising PCR inhibitors that may be present in the biological material.

Further according to the invention, the biological material captured on the capturing scaffold may be air dried and stored at ambient temperature.

The capturing scaffold may be pre-treated chemically and/or physically prior to the capturing of the biological material. It is foreseen that a batch of capturing scaffolds may be pre-prepared and stored for later use.

The capturing scaffold chemically may be pre-treated with a cross-linking agent selected from the group consisting of ethyldimethylaminopropyl carbodiimide (EDC), N,N'-dicyclohexylcarbodiimide (DCC), N,N'-diisopropylcarbodiimide (DIC), 1-cyclohexyl-3-(2-morpholinyl-(4)-ethyl)carbodiimide metho-p-toluenesulfonate (CMC), aldehyde and combinations thereof.

The step of pre-treating the capturing scaffold physically may include the further step of increasing the outer surface area of the capturing scaffold.

The step of pre-preparing the capturing scaffold chemically and/or physically may include the further steps of washing the treated capturing scaffold with Tris buffer (containing NaCl, a non-ionic surfactant and emulsifier derived from polyethoxylated sorbitan and oleic acid), de-ionised water, phosphate buffer containing a non-ionic surfactant emulsifier and combinations thereof.

The capturing scaffold may be selected from the group consisting of nano- or micro-particles and a body of a polymeric material.

The nano-particles may be prepared from polylactic acid or chitosan derivatives.

The polymeric material may be selected from the group consisting of polyethylene, polystyrene, polypropylene, polyvinyl chloride, nylon, teflon (poly tetra polyethylene), polychloroprene, polyacrylonitrile, preferably modified polystyrene.

It was found that a capturing scaffold in the form of a sheet or strip of modified polystyrene works particularly well for capturing the biological material and for subsequently storing, transporting and/or analysing the biological material.

According to a second aspect of the invention there is provided a biological material captured on a capturing scaffold using the method of the first aspect of the invention.

According to a third aspect of the invention there is provided a capturing scaffold for capturing a biological sample, prepared using a method as hereinbefore described.

According to a fourth aspect of the invention there is provided a kit for use in a method of preparing biological material from a biological sample selected from the group consisting of blood and sputum samples, the kit comprising:
- a capturing scaffold according to the third aspect of the invention; and
- a lysis buffer containing a solubilising agent and a detergent for simultaneously lysing the biological sample to make the biological sample available, inhibiting coagulation of the biological sample, and capturing at least one fraction of the biological material on the capturing scaffold.

DESCRIPTION OF THE DRAWING

The invention is described in more detail below also at the hand of the enclosed drawing (FIG. 1) which illustrates an adaptation of the lysis micro reactor ('LMR') or processing device 10 as described in the '536 application, the content of which is incorporated herein by reference.

DESCRIPTION OF PREFERRED EMBODIMENTS OF THE INVENTION

According to a preferred embodiment of the invention there is provided a method of preparing biological material from a biological sample in the form of a blood sample, the method including the steps of altering the constitutive characteristics of the blood sample in the presence of a capturing scaffold by concomitantly:
- adding a lysis buffer containing a solubilising agent, a detergent and a reducing agent to the blood sample;
- elevating the temperature of the blood sample above 40 degrees Celsius and up to a 100 degrees Celsius, preferably 92 degrees Celsius; and
- physically treating the blood sample through agitation, for simultaneously:
  - inhibiting coagulation of the blood sample;
  - lysing the blood sample to release the biological material from the blood sample, thus making the biological material available; and
  - capturing at least one fraction of the biological material on the capturing scaffold.

Subsequently the capturing scaffold, with the particular fraction of biological material captured thereon, is removed from the remainder of the blood sample and washed with de-ionised water. The capturing scaffold is subsequently stored, transported or presented for analysis of the biological sample.

Purified starch such as purified corn or potato starch is optionally added to the biological material simultaneously with the lysis buffer for neutralising any PCR inhibitors that may be present in the biological material.

The solubilising agent comprises a chaotropic salt in the lysis buffer. The lysis buffer is selected from the group consisting of phosphate buffers, 4-(2-hydroxyethyl)-1-piperazineethanesulfonic acid (HEPES), N-Cyclohexyl-2-aminoethanesulfonic acid (CHES), N-cyclohexyl-3-aminopropanesulfonic acid (CAPS) and piperazine-N,N-bis(2-ethanesulfonic acid) (PIPES), Tris-HCl, as well as other tris(hydroxymethyl)aminomethane (Tris) buffers containing ethylene diamine tetra-acetic acid (EDTA), ethylene glycol tetra-acetic acid (EGTA), deoxycholate, sodium chloride (NaCl), sodium phosphate, octylphenoxypolyethoxyethanol, and non-ionic surfactants provided with a hydrophilic polyethylene oxide group and a hydrocarbon lipophilic or hydrophobic group, and combinations thereof. The lysis buffer has a pH of between 4 and 9, preferably 7.5.

The chaoropic salt is selected from the group consisting of urea, thiourea, guanidine hydrochloride, lithium perchlorate, sodium iodine, sodium perchlorate, guanidine isothiocyanate, guanidine carbonate, guanidine thiocyanate, derivatives thereof, preferably guanidine hydrochloride and combinations thereof.

The detergent is selected from the group consisting of 3-[(3-cholamidopropyl)dimethylammonio]-1-propanesulfonate (CHAPS), a nonionic surfactant and emulsifier derived from polyethoxylated sorbitan and oleic acid, a nonionic surfactant which has a hydrophilic polyethylene oxide group and a hydrocarbon lipophilic or hydrophobic group, saponin, sodium deoxycholate, SDS, octyl glucoside, octyl thioglucoside, laurly maltose, octylphenoxypolyethoxyethanol, and combinations thereof.

The reducing agent is selected from the group consisting of 2-mecarptoethanol, dithiothreitol (DTT), 2-mercaptoethylamine, Tris(2-carboxyl)phosphine (TCEP), cysteine HCl, N-ethylmaleimide, Nacystelyn, dornase alfa, thymosin $\beta_4$, guaifenesin TCEP HCl, and combinations thereof.

The capturing scaffold is selected from the group consisting of nano- or micro-particles and a body of a polymeric material.

The polymeric material is selected from the group consisting of polyethylene, polystyrene, polypropylene, polyvinyl chloride, nylon, teflon (poly tetra polyethylene), polychloroprene, polyacrylonitrile, silicones, preferably modified polystyrene.

The step of providing a capturing scaffold includes the further step of chemically and/or physically preparing the capturing scaffold, preferably in the form of a strip of modified polystyrene. The method of preparing the capturing scaffold chemically includes the step of pre-treating the capturing scaffold with a cross-linking agent selected from the group consisting of ethyldimethylaminopropyl carbodiimide (EDC), N,N'-dicyclohexylcarbodiimide (DCC), N,N'-diisopropylcarbodiimide (DIC), 1-cyclohexyl-3-(2-morpholinyl-(4)-ethyl)carbodiimide metho-p-toluenesulfonate (CMC), aldehyde and combinations thereof. The step of preparing the capturing scaffold chemically includes the further step of washing the treated capturing scaffold with Tris buffer, de-ionised water, non-ionic detergent and combinations thereof.

The capturing scaffold is further pre-treated physically to increase the outer surface area of the capturing scaffold.

The prepared biological material captured on the capturing scaffold is subsequently air dried and stored at ambient temperature.

Example

Detailed Description of Respective Steps in the
Method According to the Invention Pre-Preparation of a Capturing Scaffold in the Form of a Modified Polystyrene Strip (19) for Use on a Method According to the Invention A capturing scaffold in the form of a polystyrene strip 19 (FIG. 1) is pre-treated by physical and chemical steps to increase the surface area of the capturing scaffold. The clear polystyrene strip (0.127 mm×1 mm×40 mm) is sanded and incubated overnight in 20 mM EDC HCl (N-[3-Dimethyl-aminopropyl]-N'-ethylcarbod iimide hydrochloride). The polystyrene strip is washed once with 10 mM Tris-buffer, pH 7.5 (150 mM NaCl and 0.05% Tween 20), and thereafter with de-ionised water.

Lysis of Blood Sample

It was found that the lysis micro reactor ('LMR') or processing device 10 as described in the '536 application could be easily adapted for use with a method according to the present invention by removably attaching the polystyrene strip 19 to the inside of the cap 18 described in the application, as illustrated in the drawing enclosed hereto as FIG. 1. The content of the specification of the '536 application is incorporated herein by reference and the same numbering of components is used herein.

An equal volume of a whole blood sample and 100 mM Tris-HCl containing 40 mM EDTA, 20 mM DTT, 4 to 6 M guanidine hydrochloride and 1 to 2% nonionic surfactant and emulsifier derived from polyethoxylated sorbitan and oleic acid (Tween 20) are simultaneously combined with the scaffold strip 19 in the mixing well 12 of the lysis micro-reactor 10, whilst lysis of the blood is achieved within 3 to 7 minutes by elevating the temperature thereof to 92 degrees Celsius and shearing (agitating) the sample using the mixing member 14 of the LMR 10. After which the modified scaffold strip 19 containing the biological material fraction in the form of DNA is removed from the well 12 by handling and removing the cap 18, without directly touching the strip 19. The prepared DNA captured on the strip 19 is used directly for analysis or air dried and stored at ambient temperature.

It was surprisingly found that by simultaneously adding the lysis buffer containing the solubilising agent, the detergent and the reducing agent to the blood sample in the presence of the capturing scaffold, combined with a concomitant increase in temperature and agitation (shearing), lysis of the blood sample is achieved within 3 to 7 minutes, with concomitant capturing of the desired fraction of the biological material on the scaffold strip 19, in a single step in a single chamber or well 12. The subsequent steps described in the '536 application are thus not required. Furthermore, it was surprisingly found that the lysis of the blood sample makes it possible for at least one fraction of the biological sample to be captured on the capturing scaffold strip 19. It was further surprisingly found that coagulation of the blood sample is inhibited, limiting interference with the capturing of the biological sample.

It was also found that the prepared biological material does not contain any components which may interfere with the fluorescent measurements, thereby allowing a direct analysis of the DNA with real-time PCR, without any further purification required.

Furthermore, it was surprisingly found that the prepared biological material captured on the scaffold strip 19 could be air dried and stored at ambient temperature for future analysis, and could be easily transported or even sent via mail if required.

It is foreseen that the required fraction of the biological material that could be captured from the blood sample could be in the form of nucleic acids (including DNA and RNA), protein, serum, cells, tissue, plasma, antigens, antibodies, or reaction products.

It is further foreseen that the method according to the invention provides a simple, relatively fast (less than 10 minutes), efficient and robust method for preparing uncontaminated biological material from a blood sample without the need to apply numerous consecutive steps that necessarily have to be taken in a laboratory environment or in different chambers of the LMR. It was found that, in particular, a kit comprising the said capturing scaffold strip and lysis buffer as described above could be prepared and provided to field workers collecting blood samples in rural areas using the LMR. The blood sample could be combined with the scaffold and lysis buffer in the LMR and the scaffold strip removed once the biological material has been captured on the scaffold strip. The advantages of this single step method over the relatively complex prior art methods requiring a laboratory environment, numerous enzymes and other reagents and multiple steps, are evident.

It was further surprisingly found that the same method, steps and reagents described herein works suitably well in respect of sputum samples. Therefore, although the preferred embodiments and samples are directed towards blood samples, it is to be understood as applying to sputum samples as well without any substantial changes to the steps or reagents.

It will be appreciated that variations in detail are possible with a method of preparing biological material for analysis according to the invention without departing from the scope of the claims.

REFERENCES

1. Boom R., Sol C. J. A. Salimans M. M. M., Jansen C. J., Wertheim van Dillen and Van der Noordaa J. (1989). Rapid and simple method for purification of nucleic acids. *J. Clin. Microbiol.* 28: 495-503.
2. Bush C., and Harvey M. (1991). Rapid isolation of genomic DNA from whole blood to borosilicate particle. *Clin Chem* 37: 1060.
3. U.S. Pat. No. 5,346,994 entitled "Shelf-stable product and process for isolating RNA, DNA and proteins", published 13 Sep. 1994, inventor, Chomczynski P.
4. US Patent Application Number 2010/0291536 entitled "Samples processing cassette system, and method", published 18 Nov. 2010, inventors Viljoen et al. ("the '536 application").

The invention claimed is:

1. A method of preparing biological material from a biological sample selected from the group consisting of blood and sputum samples, the method including the step of altering at least one constitutive characteristic of the biological sample in the presence of a capturing scaffold by adding a lysis buffer containing a solubilising agent in the form of a chaotropic salt selected from the group consisting of urea, thiourea, guanidine hydrochloride, lithium perchlorate, sodium iodine, sodium perchlorate, guanidine isothiocyanate, guanidine carbonate, guanidine thiocyanate, derivatives of said chaotropic salts and combinations thereof and a detergent to the biological sample, and concomitantly adding purified starch to the biological material together with the lysis buffer for neutralising any PCR inhibitors present in the biological material, and concomitantly physically treating the biological sample through agitation and elevating the temperature of the biological sample above 40 degrees Celsius and up to a 100 degrees Celsius; for simultaneously:

inhibiting coagulation of the biological sample;

lysing the biological sample to release biological material from the biological sample thus making the biological material available; and capturing at least one fraction of the biological material on the capturing scaffold in a single chamber or well such that the biological material captured on the capturing scaffold is usable directly for analysis without any purification required and wherein the biological material captured on the capturing scaffold can be subsequently air dried and stored at ambient temperature.

2. A method according to claim 1 including the subsequent step of removing the capturing scaffold together with the captured fraction of the biological sample from the remainder of the biological sample.

3. A method according to claim 1 wherein the concentration of the chaotropic salt in the lysis buffer is in the range of from 2 M to 8 M.

4. A method according to claim 1 wherein the lysis buffer is selected from the group consisting of phosphate buffers, 4-(2-hydroxyethyl)-1 -piperazineethanesulfonic acid (HEPES), N-Cyclohexyl-2-aminoethanesulfonic acid (CHES), N-cyclohexyl-3-aminopropanesulfonic acid (CAPS) and piperazine-N/, N-bis(2-ethanesulfonic acid) (PIPES), Tris-HCl, as well as other tris(hydroxymethyl) aminomethane (Tris) buffers containing ethylene diamine tetra-acetic acid (EDTA), ethylene glycol tetra-acetic acid (EGTA), deoxycholate, sodium chloride (MCl), sodium phosphate, octylphenoxypolyethoxyethanol, and non-ionic surfactants provided with a hydrophilic polyethylene oxide group and a hydrocarbon lipophilic or hydrophobic group, and combinations thereof.

5. A method according to claim 4 wherein the lysis buffer has a pH of between 4 and 12.

6. A method according to claim 1 wherein the detergent is selected from the group consisting of 3-[(3-cholamidopropyl) dimethylammonio]-1-propanesulfonate (CHAPS), a nonionic surfactant and emulsifier derived from polyethoxylated sorbitan and oleic acid, a nonionic surfactant which has a hydrophilic polyethylene oxide group and a hydrocarbon lipophilic or hydrophobic group, saponin, sodium deoxycholate, SDS, octyl glucoside, octyl thioglucoside, laurly maltose, octylphenoxypolyethoxyethanol, and combinations thereof.

7. A method according to claim 6 wherein the detergent has a concentration of between 0.3% and 6%.

8. A method according to claim 1 wherein the biological material is captured in the form of nucleic acids, protein, serum, cells, tissue, plasma, antigens, antibodies, or reaction products.

9. A method according to claim 1 including the step of concomitantly adding a reducing agent selected from the group consisting of 2-mecarptoethanol, dithiothreitol (DTT), 2- mercaptoethylamine, tris(2-carboxyl)phosphine (TCEP), cysteine HCl N-ethylmaleimide, Nacystelyn, dornase alfa, thymosin β4, guaifenesin TCEP HCl, and combinations thereof, to the biological sample together with the lysis buffer containing the solubilising agent and the detergent.

10. A method according to claim 1 wherein the capturing scaffold is treated chemically and/or physically prior to the capturing of the biological material such that a batch of capturing scaffolds is pre-prepared and stored for later use.

11. A method according to claim 10 wherein the step of pre-treating the capturing scaffold physically includes the further step of increasing the outer surface area of the capturing scaffold.

12. A method according to claim 10 wherein the capturing scaffold is chemically pre-treated with a cross-linking agent selected from the group consisting of ethyldimethylaminopropyl carbodiimide (EDC), N,N'-dicyclohexylcarbodiimide (DCC), N,N'-diisopropylcarbodiimide (DIC), 1-cyclohexyl-3-(2-morpholinyl-(4)-ethyl)carbodiitnide metho-p-toluenesulfonate (CMC), aldehyde and combinations thereof.

13. A method according to claim 10 wherein the step of pre-preparing the capturing scaffold chemically and/or physically includes the further steps of washing the treated capturing scaffold with Tris buffer (containing NaCl, a non-ionic surfactant and emulsifier derived from polyethoxylated sorbitan and oleic acid), de-ionised water, phosphate buffer containing a non-ionic surfactant emulsifier and combinations thereof.

14. A method according to claim 1 wherein the capturing scaffold is selected from the group consisting of nano- or micro-particles and a body of a polymeric material.

15. A method according to claim 14 wherein the nanoparticles are prepared from polylactic acid or chitosan derivatives.

16. A method according to claim 14 wherein the polymeric material is selected from the group consisting of polyethylene, polystyrene, polypropylene, polyvinyl chloride, nylon, teflon (poly tetra polyethylene), polychloroprene and polyacrylonitrile.

* * * * *